United States Patent [19]

Motohiro et al.

[11] Patent Number: 5,698,988
[45] Date of Patent: Dec. 16, 1997

[54] METHOD AND DEVICE OF DETECTING A DETERIORATION

[75] Inventors: Tomoyoshi Motohiro, Seto; Yoshiyuki Sakamoto, Nisshin; Koji Yokota, Nagoya, all of Japan

[73] Assignee: Kabushiki Kaisha Toyota Chuo Kenkyusho, Aichi-ken, Japan

[21] Appl. No.: 676,813

[22] Filed: Jul. 8, 1996

[30] Foreign Application Priority Data

Jul. 6, 1995 [JP] Japan ................................. 7-171181
Jul. 1, 1996 [JP] Japan ................................. 8-171340

[51] Int. Cl.$^6$ ............................................. G01N 15/00
[52] U.S. Cl. ................... 324/719; 324/765; 324/718; 437/8
[58] Field of Search ................... 324/765, 719, 324/525, 718, 715; 437/8

[56] References Cited

U.S. PATENT DOCUMENTS

| | | | |
|---|---|---|---|
| 3,974,443 | 8/1976 | Thomas | 324/716 |
| 4,100,486 | 7/1978 | Casowitz | 324/719 |
| 4,144,493 | 3/1979 | Lee | 324/765 |
| 5,051,690 | 9/1991 | Maly | 437/8 |
| 5,082,792 | 1/1992 | Pasch | 437/8 |

Primary Examiner—Vinh P. Nguyen
Assistant Examiner—Jose M. Solis
Attorney, Agent, or Firm—Oblon, Spivak, McClelland, Maier & Neustadt, P.C.

[57] ABSTRACT

A method and device of readily detecting deterioration of a sample at low cost, which do not require any maintenance and monitoring of the sensor properties, and accordingly can decrease a load assigned to a system side. A conductive sensor having a pair of electrodes and a conductive film which is disposed between the pair of electrodes and is composed of a conductive material formed in a continuous region so as to connect the pair of electrodes at least electrically in its initial state is placed in an atmosphere where the sample is placed. The percolation transition of the conductive material of the conductive film occurs due to the grain growth thereof, accompanied by the deterioration of the inorganic material composing the sample due to the grain growth thereof. By monitoring the variation in electric resistance of the conductive sensor due to the percolation transition of the conductive material, the deterioration of the sample can be detected.

12 Claims, 10 Drawing Sheets

SIDE ELEVATIONAL VIEWS IN THE DIRECTION OF P

SIDE ELEVATIONAL VIEWS IN THE DIRECTION OF Q

METHOD AND DEVICE OF DETECTING A DETERIORATION

BACKGROUND OF THE INVENTION

1. Field of the Invention

The present invention relates to a method and device of detecting the deterioration of an inorganic material, which can be used to detect the deterioration of a catalyst for purifing exhaust gases, an inside wall of a blast furnaurnace, boiler and incinerator, or the like.

2. Description of the Related Art

Conventionally, a combustion-type gas sensor has been used for detecting the deterioration of a catalyst to purify exhaust gases. In this detecting method, the gas sensor detects the concentration of combustible components within an emission after contacting the catalyst, and determines the deterioration thereof from the detected result. This method has advantages that a voltage output proportional to the gas concentration can be obtained and that there is hardly any influence by environmental temperature, humidity and carbon dioxide gases. This method has been successfully practiced for a long time in chemical plants or the like.

The method using the combustion-type gas sensor, however, has a defect that when the concentration of combustible components is about 100 ppm, the output voltage is as low as 1 mV. In addition, a response time is as long as several seconds, and the sensor itself deteriorates with the passage of time.

Accordingly, in order to improve the method of detecting the deterioration of a catalyst, several methods can be contemplated. They, however, have various problems as follows:

1) The lifetime of the catalyst is determined by the total accumulated 'stress' given to the catalyst by the history of temperature and atmospheric gas during its lifetime. By measuring the temperature and atmospheric gas within a catalyst converter continuously, the lifetime of the catalyst can be estimated by calculating the total accumulated 'stress' from the total history of the measured data. This method, however, has problems that a large computing load would be assigned to a system side, and the cost would be increased.

2) By measuring the temperatures and atmospheres of both the upstream and downstream of a catalytic converter continuously, the deterioration of the catalyst can be determined from the difference therebetween and the variation of a dynamic response, and give the alarm. However, it would be technically difficult to make the measured data correspond to the actual deterioration of the catalyst, because of the difference in operation mode or the like.

3) The methods 1) and 2) in which the temperature and atmosphere are measured continuously by using a sensor poses a problem of how to detect the deterioration of the sensor itself. The detection of the deterioration of the sensor itself would assign a considerable load to the system side. If sensor can have a lifetime much longer than that of the catalyst, the replacement of the sensor would not be needed upon replacing the catalyst. Accordingly, the sensor need be installed separately from the catalyst so as not to obstruct the replacement of the catalyst, and the cost of removing and installing the sensor need be taken into consideration.

SUMMARY OF THE INVENTION

It is an object of the present invention to provide a method and device of detecting the deterioration of a sample to be detected, which are capable of readily detecting the deterioration without requiring any maintenance and monitoring of the sensor properties, accordingly with a reduced load assigned to a system side, and at low cost.

The present inventors have made intensive researches on the method and device of detecting the deterioration of a catalyst based on the technical idea that the deterioration of the catalyst for purifing exhaust gases is caused mainly by the grain growth of noble metals carried as a catalyst, and have contemplated a method and device of detecting the deterioration of the catalyst using the percolation transition caused by the grain growth of metals, thus completing the present invention.

The method of the present invention is directed to the method of detecting the deterioration due to the grain growth in an inorganic material constituting a sample body. The method includes the steps of placing a conductive sensor in an atmosphere where the sample is placed, the conductive sensor comprising a pair of electrodes and a conductive film disposed between the pair of electrodes, the conductive film being composed of a conductive material formed in a continuous region for connecting electrically the pair of electrodes at least in an as-prepared state, and monitoring variation of an electric resistance of the conductive sensor which is caused by the percolation transition of the conductive material due to the grain growth therein accompanied with the deterioration of the inorganic material.

The device of the present invention is directed to the device for detecting the deterioration due to the grain growth in an inorganic material constituting a sample body. The device has a conductive sensor comprising a pair of electrodes and a conductive film disposed between the pair of electrodes, the conductive film being composed of a conductive material formed in a continuous region, for connecting electrically the pair of electrodes at least in an as-prepared state, and having abrupt increase in the electric resistance due to the percolation transition in the conductive material in a predetermined deterioration state of the inorganic material caused by the grain growth in the conductive material accompanied by deterioration of the inorganic material.

The inorganic material for the sample is not limited to a specific material. Any inorganic material can be used provided that the deterioration thereof can be considered to be caused mainly by the grain growth thereof. Examples thereof include metals, semiconductors, inorganic compounds and composite materials thereof.

The conductive material is not limited to a specific material. Any conductive material can be used provided that it electrically connects the electrodes at least in an as-prepared state and that the grain growth of the conductive material occurs with the deterioration of the inorganic material composing the sample followed by the percolation transition, which causes the break down or partial break down of the conductive film composed of the conductive material and the adrupt increase of the electric resistance thereof. Examples thereof include metals, semiconductors, conductive inorganic compounds and semiconductor organic compounds.

The "monitoring" hereindescribed means to grasp the break down or the change in the electric resistance, for example, to determinate, detect and watch the break down or the change in the electric resistance.

The percolation transition generally means that the composite material of an insulating material and a conductive material transfers from an insulator to a conductor or vice versa at a predetermined volume ratio of the insulating material to the conductive material. Furthermore, the percolation transition herein means that at the volume ratio near a critical volume ratio, the conductive material coagulates due to the history of temperature and atmosphere causing the coagulated materials isolated from each other like islands within the insulating material as a matrix. The percolation transition defined here, that is, accompanies the sudden loss of the conductive properties and the remarkable increase in the electric resistance.

In a preferred embodiment, the inorganic material composing the sample is noble metals, and the conductive material of the conductive sensor is identical to the inorganic material composing the sample.

The conductive sensor may include a plurality of pairs of electrodes and a plurality of conductive films formed between the electrodes and having different thicknesses. Alternatively, the conductive sensor may include a pair of electrodes and a pluality of conductive films formed between the electrodes in parallel and having different thicknesses. In this case, the conductive films which are formed in parallel may be spaced from or contacted with each other.

The method and device of the present invention have been contemplated based on the technical assumption that the deterioration of a sample is caused mainly by the grain growth of the inorganic material composing the sample.

In the method and device of the present invention, the conductive sensor includes electrodes and conductive films composed of the conductive material which is formed in a continuous region to connect electrically the electrodes at least in an as-prepared state.

With the present invention, by monitoring the variation in electric resistance of the conductive sensor which is disposed in an atmosphere where the sample is placed, the deteriorated state of the sample is detected. The conductive sensor includes electrodes and conductive films composed of the conductive material which is formed in a continuous region to connect the electrodes at least electrically in an initial state thereof. Thus, conductive sensor exhibits the conductive properties in the initial state thereof. The grain growth of the conductive material occurs due to the history of temperature and atmosphere gas, to which the inorganic material composing the sample is also subjected. When the grain growth of the conductive material reaches a predetermined stage depending on the physical properties and ratio of the conductive material composing the conductive film, or the film thickness thereof or the like, the percolation transition of the conductive material occurs to vary the electric resistance of the conductive film composed of the conductive material. By monitoring the resultant electric resistance of the conductive sensor, the deterioration of the sample can be detected.

With the present invention, in order to detect a predetermined deterioration of the sample, the physical properties and ratio of the conductive material constituting the conductive film or the film thickness thereof or the like are adjusted such that the percolation transition of the conductive material occurs at the predetermined deterioration of the sample.

In the present invention, by varying the film thickness of the conductive film, the time required until occurrence of the break down thereof due to the percolation transition of the conductive material can be adjusted. Namely, there is a correlation between the film thickness of the conductive film and the time required until occurrence of the break down thereof. As the film thickness of the conductive film reduces, the time required until occurrence of the break down of the conductive film is shortened. Therefore, with the arrangement that the conductive sensor is composed of a plurality of pairs of electrodes and a plurality of conductive films having different thicknesses, which are respectively formed between the plurality of pairs of electrodes, or that the conductive sensor is composed of one pair of electrodes and a plurality of conductive films having different thicknesses, which are formed in parallel between the electrodes, when the film thicknesses of the conductive films increases successively from one end of the conductive sensor to the other end thereof, for example, the conductive films can break down due to the percolation transition of the conductive material successively from the one end of the conductive sensor to the other end thereof.

Other objects, features, and characteristics of the present invention will become apparent upon consideration of the following description and the appended claims with reference to the accompanying drawings, all of which form a part of this specification.

DETAILED DESCRIPTION OF PREFERRED EMBODIMENTS

Figure 1:
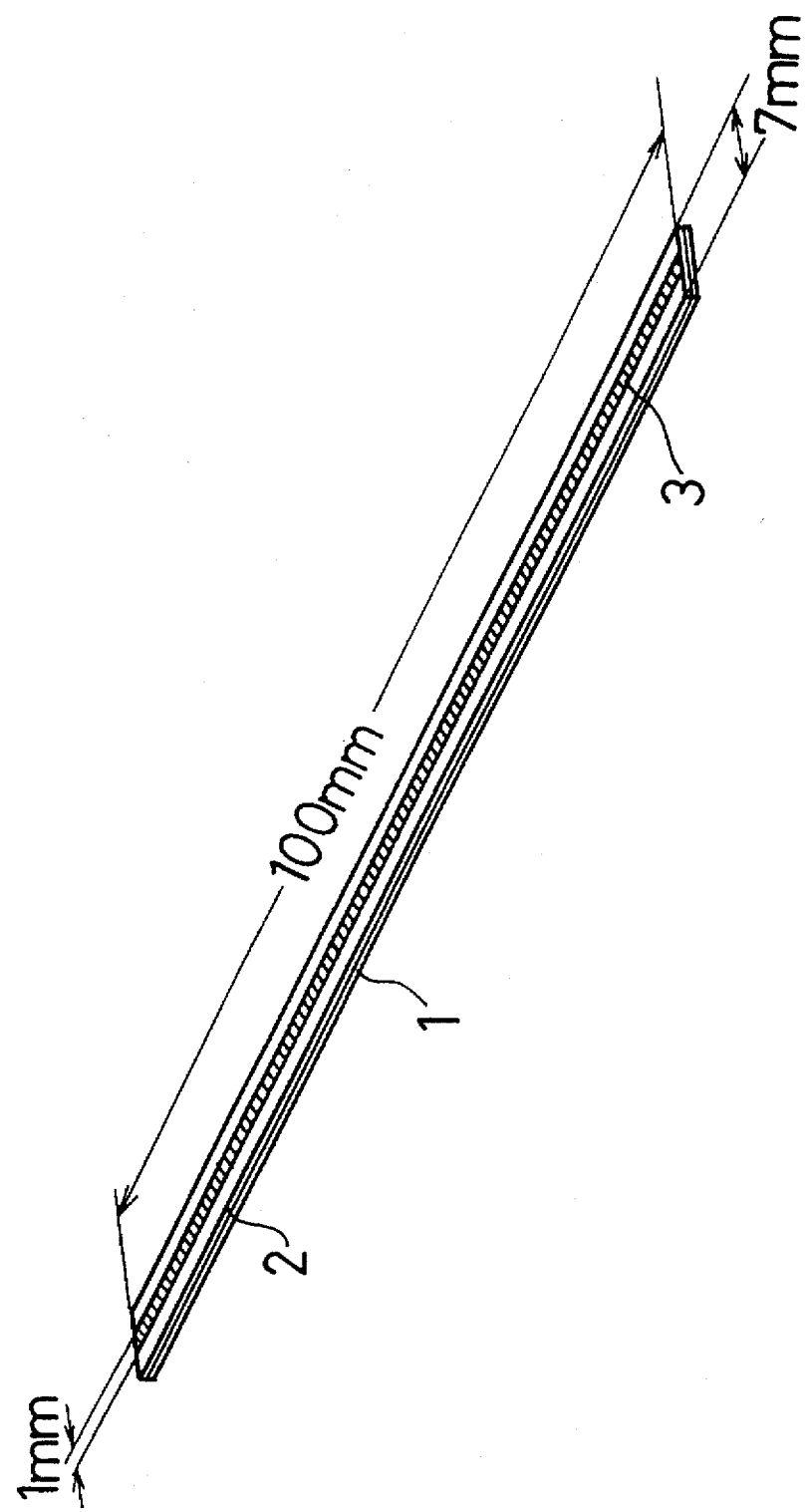
FIG. 1 is a perspective view of a substrate used in a first embodiment of a deterioration detecting device in accordance with the present invention.

First embodiment:

As shown in FIG. 1, an upper surface of a substrate 1 made of sintered $ZrO_2$, which was 7 mm in width, 100 mm in length, and 1 mm in thickness, was coated with a γ-alumina coat layer 2 containing cerium oxide and lanthanum oxide, like a three way catalyst for a motor vehicle, to a thickness of 50 μm by a wash coat method. This layer 2 provides an under-coating identical to the under-coating (carrier) for noble metals in the three way catalyst of which the deterioration is to be detected. An entire rear surface of the substrate 1 which was not coated with the γ-alumina coat layer 2, and a region extending along a longitudinal central line of an upper surface of the γ-alumina coat layer 2 with a width of 1 mm were masked with kapton tapes (composed of polyimide) 3.

Figure 2:
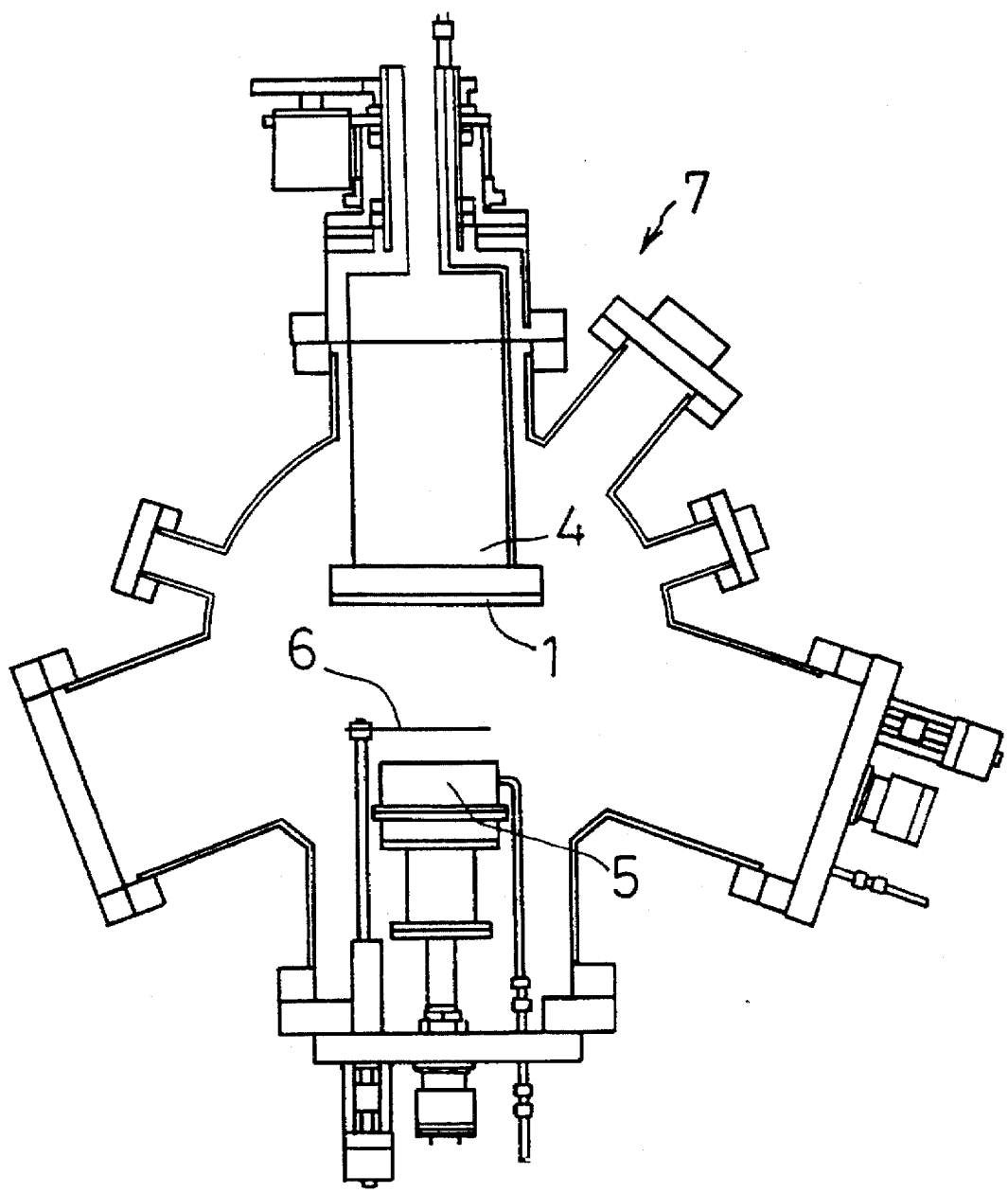
FIG. 2 is a schematic view showing the vacuum evaporation of platinum electrodes onto the substrate in the first embodiment.

As shown in FIG. 2, a sputter-deposition apparatus 7 was prepared. A holder 4 was provided at a ceiling thereof. A planar magnetron type sputter source 5 was provided at a bottom thereof so as to face the holder 4. And a shutter 6 was provided over the sputter source 5. The substrate 1 was held by the holder 4, and a platinum target having a diameter of 2 inches and a thickness of 1 mm was provided in the sputter source 5. Then, the sputter-deposition apparatus 7 was evacuated to $5.6 \times 10^{-6}$ Torr, and Ar gas was introduced to $3.2 \times 10^{-3}$ Torr. While rotating the holder 4 in this state, a radio freqency electric power of 13.56 MHz and 250 W was applied to the sputter source 5, and glow discharge was started with a reflection power of 9 W. After 20 minutes, glow discharge was stopped. Then, the sputter-deposition apparatus 7 was opened to the atmosphere, and the substrate 1 was taken out from the apparatus 7. And the kapton tapes 3 were removed from the substrate 1. As a result, the regions which had not been covered with the kapton tapes 3 showed a platinum-like tone.

Figure 3:
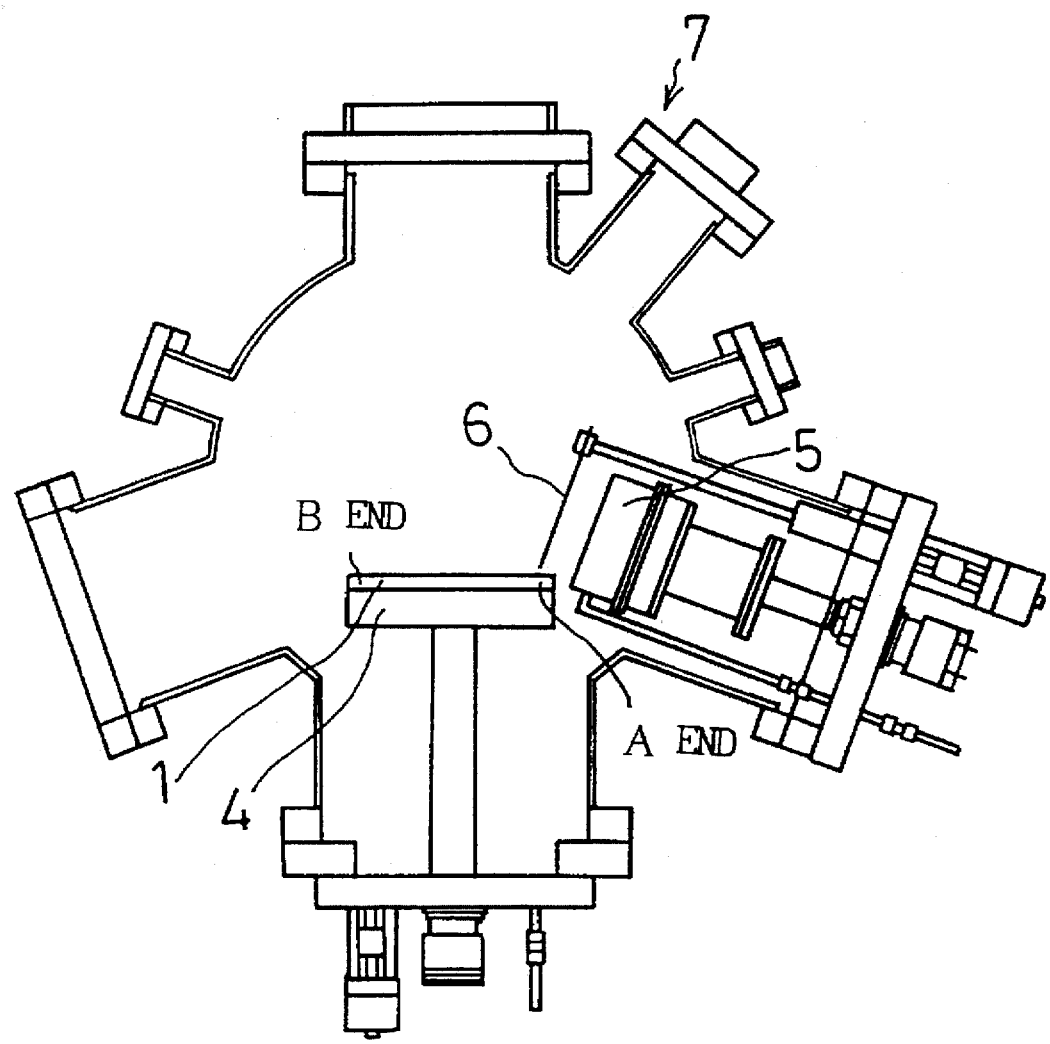
FIG. 3 is a schematic view showing the vacuum evaporation of a platinum-rhodium film as a conductive film onto the substrate in the first embodiment.

Next, another sputter-deposition apparatus 7 was prepared. As shown in FIG. 3, a holder 4 was provided at a bottom of the apparatus 7, a planar magnetron type sputter source 5 was provided adjacent to the holder 4 in a tilting relation therewith, and a shutter 6 was provided to cover an upper part of the sputter source 5. The substrate 1 having a platinum-sputtered film was held by the holder 4. A platinum-rhodium alloy target having a diameter of 2 inches and a thickness of 1 mm was provided in the sputter source 5. The sputter-deposition apparatus 7 was evacuated to $2.3 \times 10^{-6}$ Torr, and Ar gas was introduced to $5.3 \times 10^{-3}$ Torr. Then, a radio frequency electric power of 13.56 MHz and 50 W was applied to the sputter source 5, and glow discharge was started. The reflection power was 1 W. After five minutes, glow discharge was stopped. Then, the sputter-deposition apparatus 7 was opened to the atmosphere, and the substrate 1 was taken out therefrom. The belt-like central region of the substrate 1 which had been covered with the Kapton tape 3 in the first sputter-deposition step showed a color similar to that of the platinum target at one end near a sputter electrode of the sputter source (hereinafter will be called A end), and was slightly grayish at an opposite end (hereinafter will be called B end), as compared to the color prior to the sputter-deposition step. Then, an end surface (side surface) of the substrate 1 was polished to remove platinum films therefrom.

Figure 4:
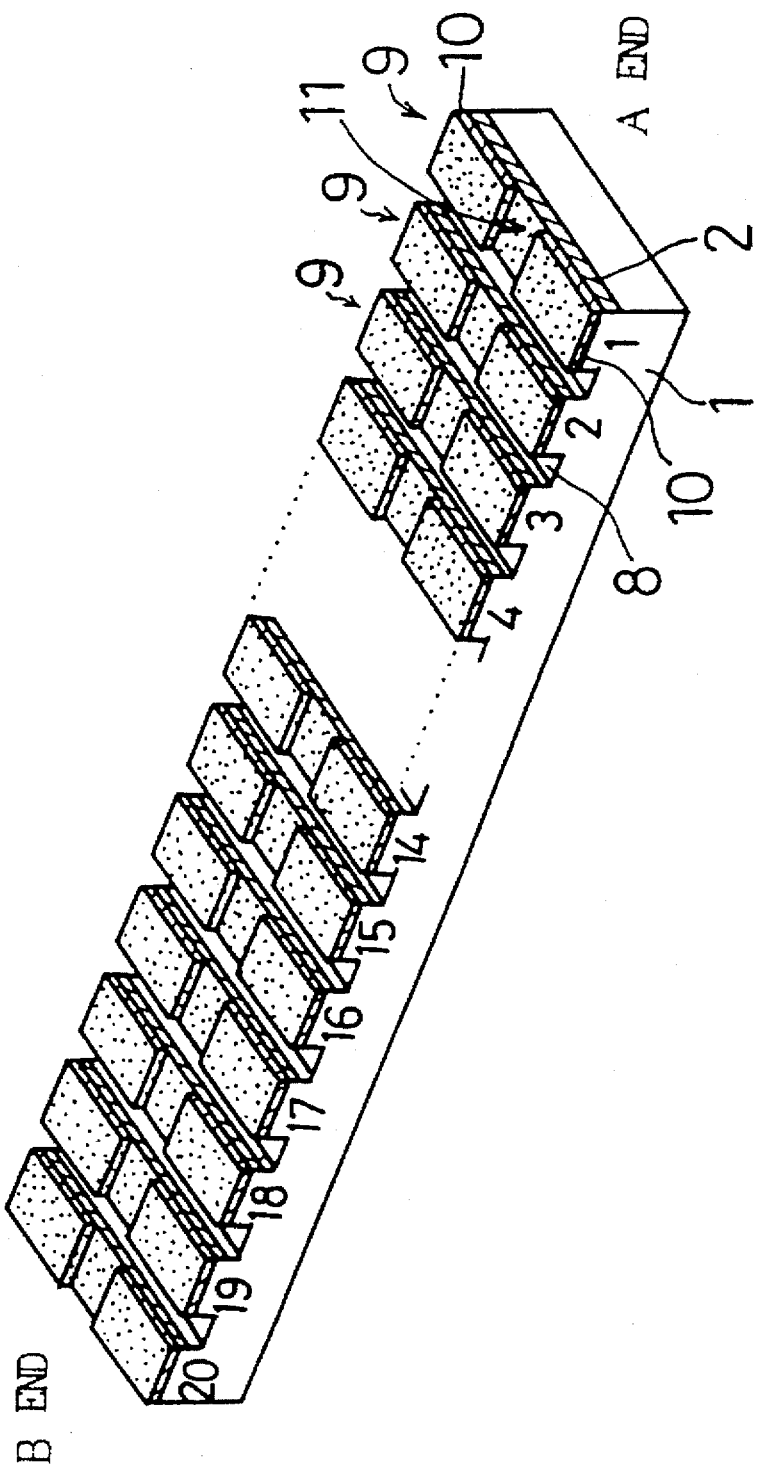
FIG. 4 is a perspective view of the deterioration detecting device in the first embodiment.

Next, as shown in FIG. 4, grooves 8 having a width of 0.5 mm were cut to a depth of 0.5 mm reaching the substrate 1 at intervals of 5 mm by a dicing machine, which results in the film on the substrate 1 being divided into twenty elements 9 isolated from each other. Each of the elements 9 was composed of the γ-alumina coat layer (thickness: 50 μm) 2, a pair of platinum electrodes (thickness: 0.5 μm) 10 which were formed on longitudinal ends of the γ-alumina coat layer 2, and a platinum-rhodium film (Pt:Rh=5:1 by wight) 11 as a conductive film, which was formed on both the longitudinally central region of the γ-alumina coat layer 2 and the platinum electrodes 10. The thickness of the platinum-rhodium film 11 of the element 9 was 0.3 μm at the A end, and 0.001 μm at the B end. The thickness of the platinum-rhodium film 11 of the sandwitched eighteen elements 9 successively decreased from the A end side to the B end side.

Figure 5:
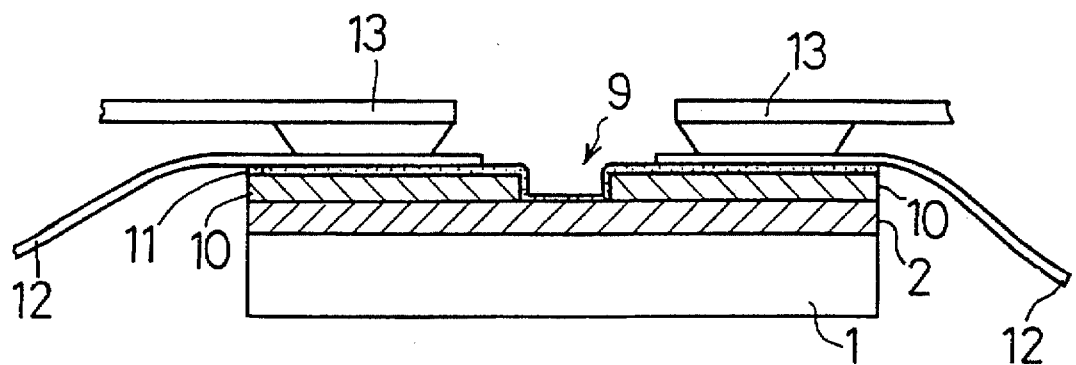
FIG. 5 is a sectional view of the deterioration detecting device in the first embodiment.

Then, as shown in FIG. 5, a pair of platinum wires 12 were secured to an upper surface of the platinum-rhodium film 11 at the positions above the platinum electrodes 10 of each of twenty elements 9 by bonding with heat and mechanically pressing with pressing members 13.

An ordinary three way catalyst for a motor vehicle was used as a catalyst of which the deterioration is to be evaluated. The ordinary three way catalyst is composed of Pt-Rh alloy (Pt:Rh=5:1 by weight), $CeO_2$ and $La_2O_3$ which are carried by γ-$Al_2O_3$ support. An inside wall of a cordierite honeycomb is coated with these materials. The thus prepared cordierite honeycomb was accommodated within a catalytic converter.

The above three way catalyst and catalyst deterioration detecting device of the present embodiment were sealed in a catalyst evaluaton device. Ends of the platinum wires 12 of each of the elements 9 were taken out of the device for monitoring the electric resistance thereof. The surface electric resistance of the element No. 1 at the A end was 135 Ω/sq., that of the element No. 20 at the B end was 3240 Ω/sq. The sandwitched eighteen elements 9 exhibited surface resistances between that of the element No. 1 and that of the element No. 20, which successively increased from the element No. 1 toward the element No. 20.

The catalyst evaluation device was heated to 1100° C. The atmosphere was repeatedly changed every five minutes from the gas composed of 0.2% of oxygen, 3.0% of carbon monoxide, 0.15% of propylene, 10.0% of vapor, and the balance being nitrogen to that composed of 4.0% of oxygen, 0.1% of carbon monoxide, 0.1% of propylene, 10.0% of vapor, and the balance being nitrogen. The hydrocarbon elimination rate with the catalyst evaluation device, namely that with the three way catalyst for a motor vehicle which was mounted thereon, is shown in TABLE 1.

TABLE 1

| Time (hr) | 1 | 2 | 5 | 10 | 20 |
| --- | --- | --- | --- | --- | --- |
| Hydrocarbon Elimination Rate (%) | 95 | 88 | 85 | 82 | 80 |

As shown in TABLE 1, the hydrocarbon elimination rate gradually decreased with the passage of time.

First, the electric resistance of the element No. 20 rapidly changed to an insulating state. Then, the electric resistances of the remaining elements Nos. 1–19 also rapidly changed to an insulating state in the order from the element most adjacent to the end B to that at the end A. The time required until the electric resistance of each element 9 rapidly increases is shown in TABLE 2 along with the initial resistance of each element.

TABLE 2

| Element No. | No. 1 | No. 2 | No. 3 | No. 4 | No. 5 |
|---|---|---|---|---|---|
| Resistance Ω/sq. | 135 | 240 | 371 | 496 | 601 |
| Resistance Increasing Time (hr) | 20 or more | 20 or more | 20 or more | 20 or more | 18.9 |

| Element No. | No. 6 | No. 7 | No. 8 | No. 9 | No. 10 |
|---|---|---|---|---|---|
| Resistance Ω/sq. | 720 | 863 | 991 | 1133 | 1302 |
| Resistance Increasing Time (hr) | 17.1 | 15.6 | 14.1 | 13.0 | 11.6 |

| Element No. | No. 11 | No. 12 | No. 13 | No. 14 | No. 15 |
|---|---|---|---|---|---|
| Resistance Ω/sq. | 1479 | 1635 | 1826 | 2003 | 2204 |
| Resistance Increasing Time (hr) | 10.66 | 9.81 | 9.01 | 8.4 | 7.78 |

| Element No. | No. 16 | No. 17 | No. 18 | No. 19 | No. 20 |
|---|---|---|---|---|---|
| Resistance Ω/sq. | 2394 | 2606 | 2799 | 3002 | 3240 |
| Resistance Increasing Time (hr) | 7.24 | 6.77 | 6.36 | 6.11 | 5.59 |

Similar experiments were also performed at 1000° C. The experimental results showed that the hydrocarbon elimination rate gently decreased, and it took a longer time for each element 9 to change to an insulating state, as compared to the case of 1100° C. However, the relation between the hydrocarbon elimination rate and the break down position of the elements 9 was not varied. These experimental results proved that the deteriorated state of the catalytic performance corresponded to the break down position of the elements 9.

Based on the above evaluation results, there could be provided a catalyst deterioration detecting device of which the elements 9 successively broke down with the decrease in hydrocarbon elimination rate of the three way catalyst. With this catalyst deterioration detecting device, by monitoring the break down of the elements 9, the decrease in hydrocarbon elimination rate of the three way catalyst can be detected.

Second Embodiment:

The present embodiment is directed to a device and method for detecting the deterioration of the three way catalyst of the first embodiment. The deterioration detecting device is provided in a zirconia sintered body known as an $O_2$ sensor.

Figure 7:
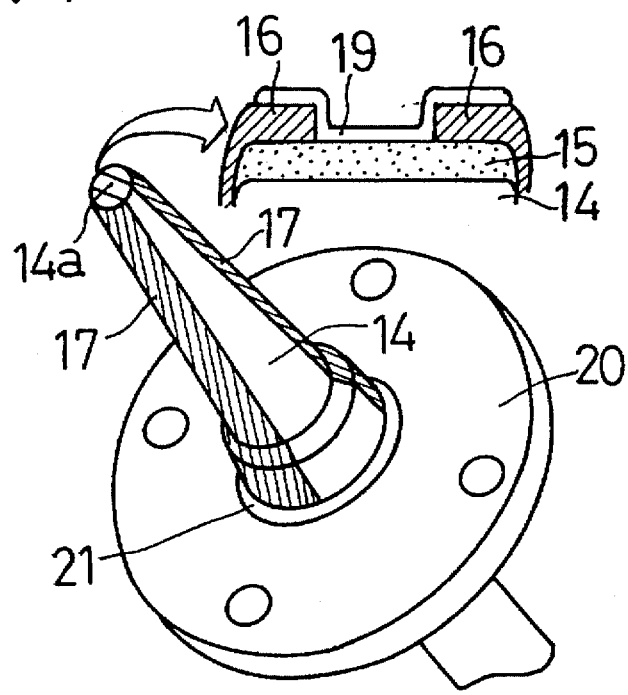
FIG. 7 is a perspective view of the deterioration detecting device in the second embodiment.

As shown in FIG. 7, a substrate 14 made of a zirconia sintered body, which had, a generally conical configuration was prepared. The top face thereof was polished to a plane having a diameter of about 2 mm. The resultant top surface 14a was coated with a γ-alumina coat layer 15 containing cerium oxide and lanthanum oxide to a thickness of 50 μm by a wash coat method as in the first embodiment. Then, platinum electrodes 16 were formed on the γ-alumina coat layer 15 in parallel by a spacing of 1 mm. Two platinum leads 17 having the width of 2 mm were formed on the side surface of the substrate 14 so as to be electrically connected to the platinum electrodes 16, respectively. These platinum electrodes 16 and platinum leads 17 were both formed by a method similar to that of a conventional $O_2$ sensor, namely, by Pt electroless plating and electroplating.

Figure 6:
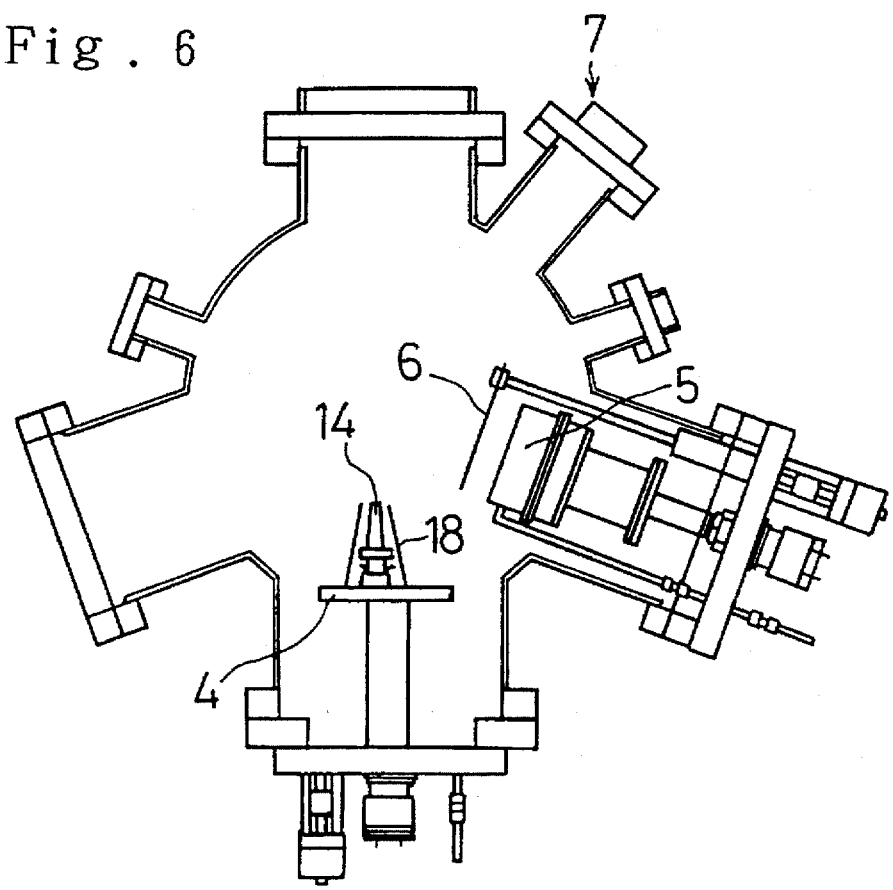
FIG. 6 is a schematic view showing the vacuum evaporating of a platinum-rhodium film as a conductive film onto a substrate in a second embodiment of a deterioration detecting device in accordance with the present invention.

Next, a sputter-deposition apparatus 7 as shown in FIG. 6 was prepared, and the substrate 14 was placed on a holder 4 at the position corresponding to that of the element 9 which broke down at a predetermined hydrocarbon elimination rate in the first embodiment, namely that of the element 9 having a platinum-rhodium film as the conductive film of a predetermined thickness. And the substrate 14 was surrounded with a protection plate 18 having a conical configuration with an upwardly opening hollow to prevent the deposition on the side surface of the substrate 14. Then, similarly to the first embodiment, a platinum-rhodium film 19 having a thickness of 0.02 μm was formed on the top surface of the substrate 14.

As shown in FIG. 7, the thus provided substrate 14 was secured to a center of an upper face of a flange 20 having a circular configuration via an insulating material 21, thus providing a flange mounted type device similar to that of the conventional $O_2$ sensor.

The thus obtained conductive sensor was mounted on the inlet side of a catalytic converter, and an accelerated durability test was performed. Practically, it was necessary to adjust the film-forming position in FIG. 6 through two or three trials and errors such that the platinum-rhodium film 19 as the conductive film broke down at a predetermined hydrocarbon elimination rate. It was confirmed that ten lots of the platinum-rhodium films broke down at the predetermined elimination rate with an error of 0.5% or less. The electric circuit for detecting the break down was very simple, and had such a construction as to detect the break down, and light a display lamp in a driver's seat, thereby informing a driver of the catalyst deterioration.

The deterioration detecting device of the present embodiment can dectect the catalyst deterioration from the deterioration (self-destruction) of the conductive sensor itself. Therefore, the maintenance and monitoring of the sensor properties are not needed.

Figure 8:
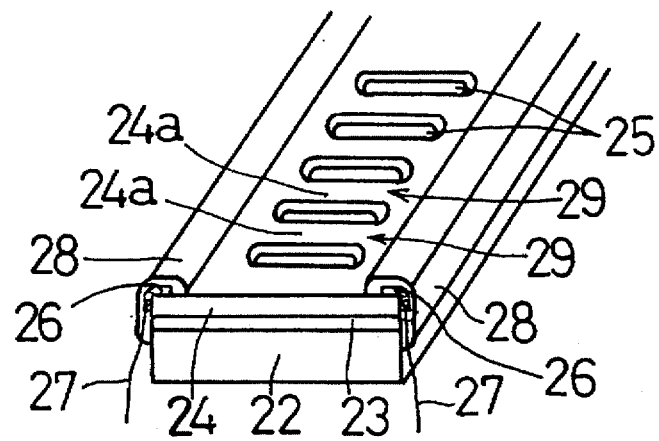
FIG. 8 is a perspective view of a third embodiment of a deterioration detecting device in accordance with the present invention.
Figure 9:
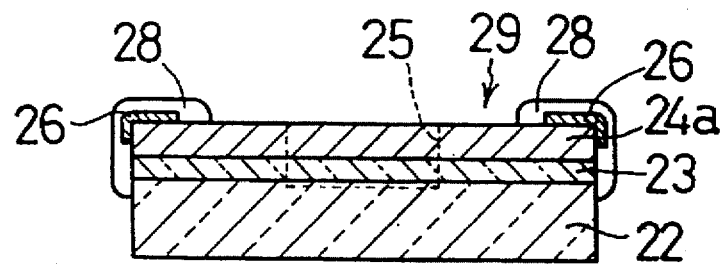
FIG. 9 is a sectional view of the deterioration detecting device in the third embodiment.

Third embodiment:

As shown in FIG. 8, a substrate 22 made of cordierite, which had a configuration identical to that of the substrate 1 of the first embodiment, was prepared, and a γ-alumina coat layer 23 was formed on an upper surface of the substrate 22, similarly to the first embodiment.

Next, the substrate 22 was held by a holder 4 of a sputter-deposition apparatus 7, similarly to the first embodiment shown in FIG. 3, and a platinum-rhodium alloy target was placed on a sputter source 5, similarly to the first embodiment. Then, similarly to the first embodiment, a platinum-rhodium film 24 were formed on an upper surface of the γ-alumina coat layer 23.

Furthermore, in the substrate 22, bottomed slots 25, each having a width of 3 mm and a depth of 0.5 mm, were formed in the part which contacts exhaust gases directly by predetermined intervals of 5 mm with a dicing machine. The bottom of each slot 25 reached the substrate 22. Platinum pieces 26 as a pair of electrodes were secured to both end edges of bridge parts 24a of the platinum-rhodium film 24, which are interposed between adjacent slots 25. One ends of lead wires 27 were electrically connected to the platinum pieces 26, respectively, and the other ends thereof were taken out of the device. Then, the platinum pieces 26 and the lead wires 27 near the platinum pieces 26 were covered with spinel solution injection films 28. Thus, twenty elements 29, each having the γ-alumina coat layer 23 which was 50 μm in thickness, the bridge part 24a of the platinum-rhodium film 24 formed on the γ-alumina coat layer 23, and the platinum pieces 26 as a pair of electrodes, which were formed on both side edges of the bridge part 24a of the platinum-rhodium film 24, were formed. The thickness of the platinum-rhodium film 24 of the element 29 was 0.3 μm at the A end, and 0.001 μm at the B end, as in the first embodiment. The sandwitched eighteen elements 29 had film thicknesses between that of the element 29 at the B end and that of the element 29 at the A end, which successively decreased from the A end side to the B end side.

The thus obtained catalyst deterioration detecting device was mounted on the upstream side of a catalytic converter. The break down of the platinum-rhodium film 24 as a conductive film was displayed with bar graphs to notify a driver of the proceeding of the deterioration of the catalyst in advance.

The bar graphs were displayed with green when the deterioration rate of the catalyst was below a standard value at which the catalyst should be replaced, with yellow when immediately behind the standard value, and with red when over the standard value.

Fourth embodiment:

The relation between the film thickness of a conductive film and the time required until occurrence of the break down of the conductive film due to the percolation transition of a conductive material was examined.

Figure 10:
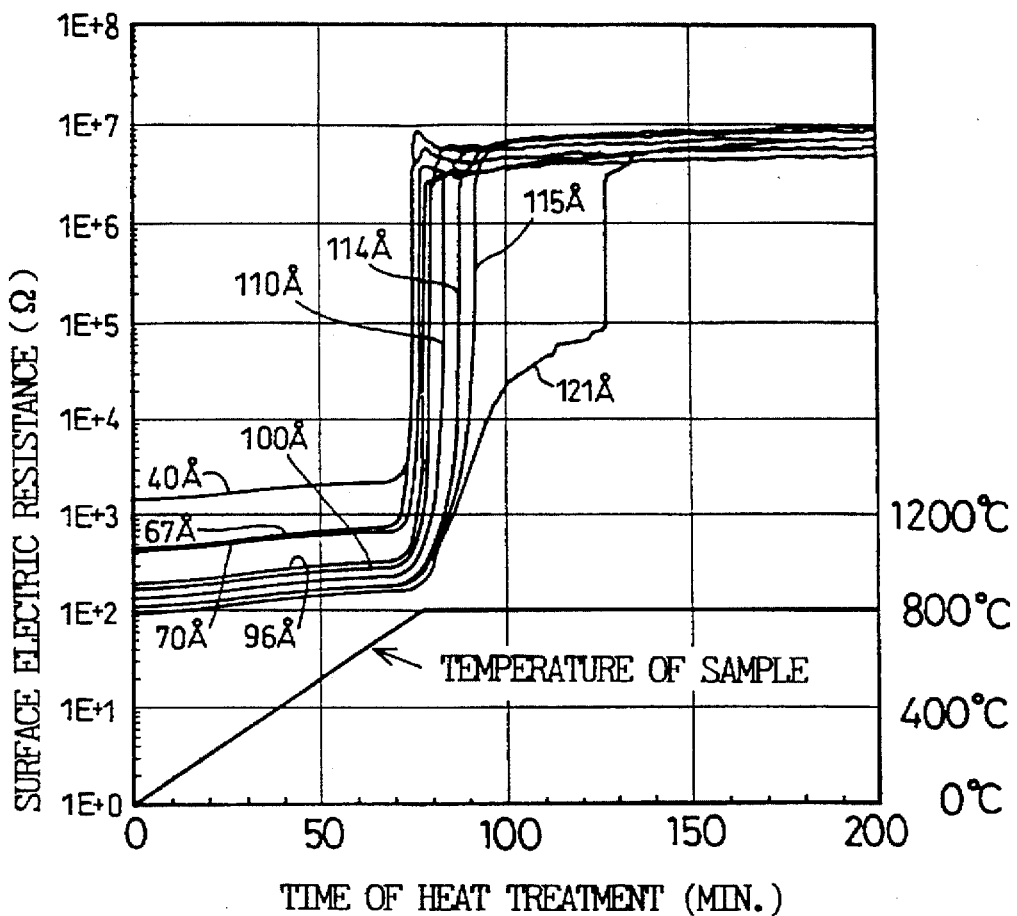
FIG. 10 is a diagram showing the relation between the film thickness of a conductive film of a fourth embodiment of a deterioration detecting device in accordance with the present invention and the time required until occurrence of the break down of the conductive film due to percolation transition of a conductive material.

First, platinum films as conductive films having different film thicknesses were respectively formed on α-alumina substrates (10 mm×10 mm, thickness: 1 mm) by a sputter-deposition apparatus 7 shown in FIG. 2, similarly to the first embodiment, thus preparing samples. Next, each sample was subjected to heat treatment in the air, and the variation in the electric resistance of each platinum film of 2 mm×2 mm was measured. The measured results are shown in FIG. 10, using the film thickness of each platinum film as a parameter. The heat treatment was carried out under the conditions that the temperature was raised up to 800° C. at a rate of 10° C. per min., and then maintained the temperature. In FIG. 10, "1E+n" means $1 \times 10^n$.

As is apparent from FIG. 10, break down of the platinum films due to percolation transition began with one having a smallest film thickness. These measured results show that the time required until occurrence of the break down of the conductive film due to percolation transition can be adjusted by varying the film thickness of the conductive film. In FIG. 10, after occurrence of the break down, the electric resistance of each sample became constant, because such electric resistance depends on conductivity of the α-alumina substrate at given temperature.

Figure 11:
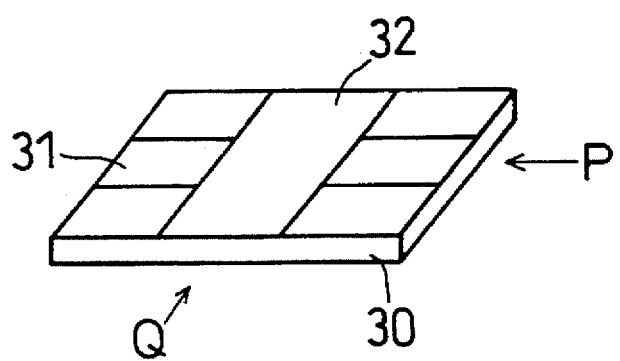
FIG. 11 is a perspective view of an α-alumina substrate with first and second polyimide tapes bonded thereto of a fifth embodiment of a deterioration detecting device in accordance with the present invention.
Figure 12:
FIGS. 12(a) through 12(f) are side elevational views taken in the direction of P of FIG. 11 showing the process of forming platinum films as electrodes and a conductive film on the α-alumina substrate of the fifth embodiment.
Figure 12:
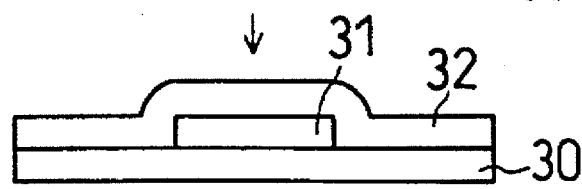
Figure 12:
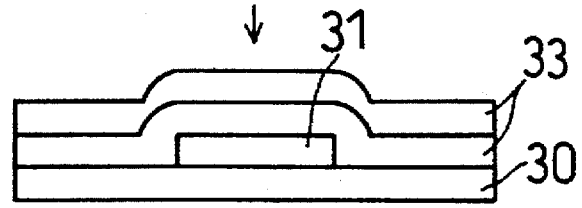
Figure 12:
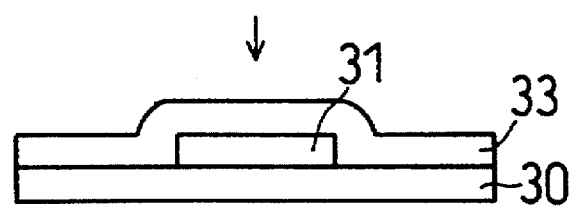
Figure 12:
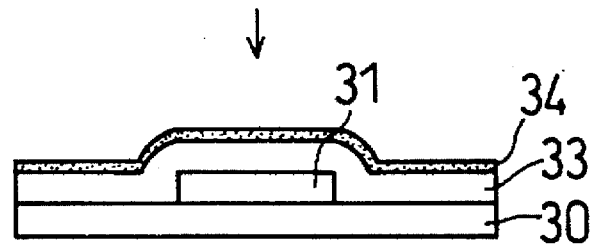
Figure 12:
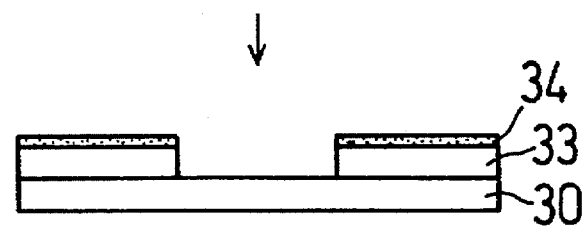
Figure 13:
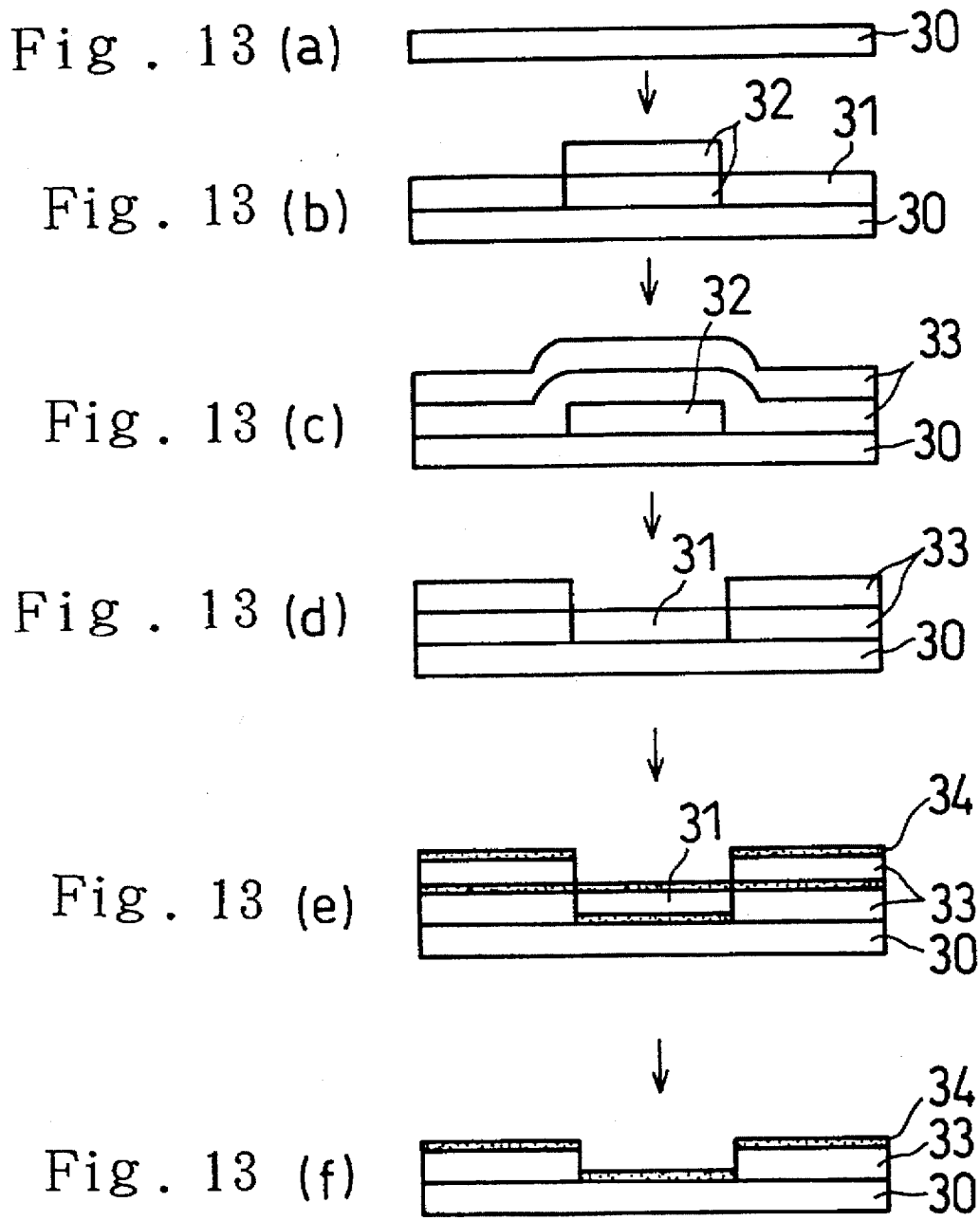
FIGS. 13(a) through 13(f) are side elevational views taken in the direction of Q of FIG. 11 showing the process of forming platinum films as electrodes and a conductive film on the α-alumina substrate of the fifth embodiment.
Figure 14:
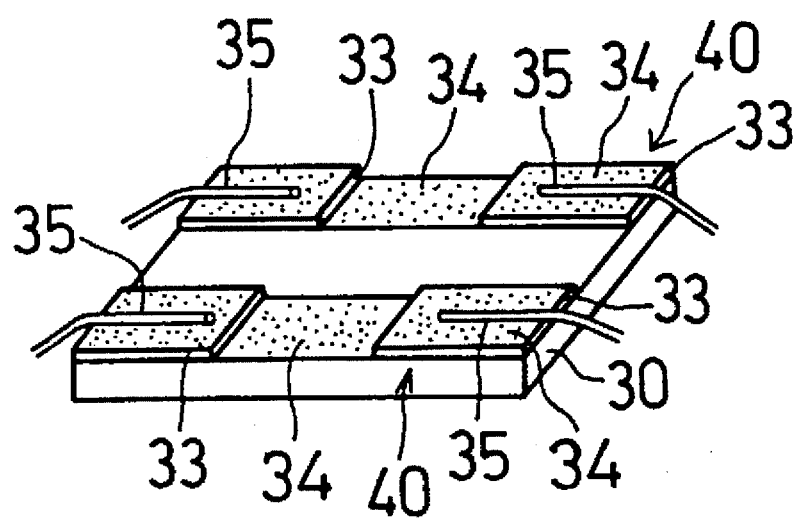
FIG. 14 is a perspective view of the α-alumina substrate of the fifth embodiment, on which two elements are formed.

Fifth Embodiment:

As shown in FIGS. 11, 12(b) and 13(b), a first polyimide tape 31 (3 mm×10 mm, thickness: 150 μm) and a second polyimide tape 32 (3 mm×10 mm, thickness: 150 μm) were bonded to a surface of an α-alumina substrate 30 (10 mm×10 mm, thickness:1 mm) in crossing relationship. FIGS. 12(a) through 12(f) are side elevational views taken in the direction of P of FIG. 11, and FIGS. 13(a) through 13(f) are side elevational views taken in the direction of Q of FIG. 11.

The α-alumina substrate 30 to which the first and second polyimide tapes 31 and 32 had been bonded was held by a holder 4 of a sputter-deposition apparatus 7, which is similar to that of the first embodiment shown in FIG. 2. A platinum target of 2 inches in diameter and 1 mm in thickness was placed on a sputter source 5. The sputtering was carried out under the conditions of $5 \times 10^3$ Torr in Ar gas pressure, 300 W in power, and 1 hour 23 minutes in discharging time. By sputtering, as shown in FIGS. 12(c) and 13(c), a platinum film 33 as electrodes having a film thickness of about 2 μm, was formed on an exposed surface of the α-alumina substrate 30, which had not been covered with the first and second polyimide tapes 31 and 32, along with surfaces of the first and second polyimide tapes 31 and 32.

Next, as shown in FIGS. 12(d) and 13(d), the second polyimide tape 32 was peeled from the α-alumina substrate 30 to lift off the platinum film 33 formed on the second polyimide tape 32. Then, the α-alumina substrate 30 was held by the holder 4 of the sputter-deposition apparatus 7, again, and the sputtering was carried out under the conditions of $5 \times 10^{-3}$ Torr in Ar gas pressure, 50 W in power, and 4 minutes in discharging time. By sputtering, as shown in FIGS. 12(e) and 13(e), a platinum film 34 as a conductive film having a film thickness of about 15 nm, was formed on an exposed surface of the α-alumina substrate 30, from which the second polyimide tape 32 had been peeled, along with the surfaces of the first polyimide tape 31 and the platinum film 33 as the electrodes.

Then, as shown in FIGS. 12(f) and 13(f), the first polyimide tape 31 was peeled from the α-alumina substrate 30 to lift off the platinum films 33 and 34 which had been formed on the first polyimide tape 31. As a result, two elements 40, each comprising a pair of platinum films 33 as the electrodes and the platinum film 34 as the conductive film formed on the surface of the pair of platinum films 33 along with the surface of the α-alumina substrate 30 between the pair of platinum films 33, were formed on the α-alumina substrate 30 with a predetermined spacing.

Finally, a pair of Pt wires 35, each having a thickness of 0.08 mm, were attached to the upper surface of the platinum film 34 as the conductive film in the part covering the platinum films 33 as the electrodes by heat pressure joining on a heated plate of 600° C. with quartz rods (not shown).

In the fifth embodiment, by bonding a plurality of first polyimide tapes 31 to a strip-shaped α-alumina substrate 30 in a longitudinal direction thereof with a predetermined spacing, and sputtering a platinum film 34 as a conductive film by the sputter-deposition apparatus 7 shown in FIG. 3, such that the film thickness of the platinum film 34 as the conductive film gradually reduces from one longitudinal end of the α-alumina substrate 30 to the other longitudinal end thereof, a plurality of elements 40, each having the platinum film 34 as the conductive film of which the film thickness gradually reduces from one longitudinal end to the other longitudinal end thereof, can be formed on the strip-shaped α-alumina substrate 30.

In the preceding embodiments, the method and device of the present invention have been applied to the detection of the deterioration of the catalyst for purifing exhaust gases. The application of the method and device of the present invention, however, are not limited. They are broadly applicable without departing from the spirit and scope of the present invention. In the preceding embodiments, platinum and rhodium have been used as both the inorganic material composing the sample of which the deterioration is to be detected and the conductive material composing the conductive film. Alternatively, other metals, semiconductors, composite materials of these materials with insulating materials may be used as both the inorganic material and the conductive material. Furthermore, in the preceding embodiments, the conductive film was composed of only the conductive material. The conductive film may be composed of both a conductive material forming a continuous region and an insulating material forming a different region. So far as conductive film have a construction that the conductive material forms a continuous region capable of connecting electrodes at least electrically in the initial state thereof.

As described above, with the method and device of the present invention, the history of temperature and atmospheric gas is accumulated within the conductive material of the conductive film composing the conductive sensor, whereby the data storage and calculation are not needed on a system side, thus enabling the detection of the deterioration with a very simple electric circuit at low cost.

In the conductive sensor of the present invention, the break down due to the grain growth (deterioration) of the conductive material, itself is the function thereof so that the maintenance of the durability, monitoring of the deterioration in properties, and compensation for properties are not needed.

Furthermore, the method and device of the present invention can detect the history of temperature or the like so that they can be used to monitor the material which would deteriorate at high temperatures. When they are applied to the blast furnace, boiler, incinator or the like, for example, the replacement time of inside walls thereof can be detected without stopping the operation thereof.

While the invention has been described in connection with what are considered presently to be the most practical and preferred embodiments, it is to be understood that the invention is not limited to the disclosed embodiments, but, on the contrary, is intended to cover various modifications and equivalent arrangements included within the spirit and scope of the appended claims.

What is claimed is:

1. A method of detecting a deterioration due to the grain growth in an inorganic material constituting a sample body, comprising the steps of:

placing a conductive sensor in an atmosphere where said sample body is placed, said conductive sensor comprising a pair of electrodes and a conductive film disposed between said pair of electrodes, said conductive film being composed of a conductive material formed in a continuous region for connecting electrically said pair of electrodes at least in an as-prepared state; and monitoring variation of an electric resistance of said conductive sensor, which is caused by the percolation transition of said conductive material due to the grain growth therein accompanied by the deterioration of said inorganic material.

2. A method as claimed in claim 1, wherein said inorganic material is noble metal.

3. A method as claimed in claim 1, wherein said conductive material is the same material as said inorganic material.

4. A method as claimed in claim 3, wherein said inorganic material is noble metal.

5. A method as claimed in claim 1, wherein said conductive sensor comprises a plurality of pairs of electrodes and a plurality of conductive films having different thicknesses, each of said plurality of conductive films being formed between each pair of said plurality of pairs of electrodes.

6. A method as claimed in claim 1, wherein said conductive sensor comprises a pair of electrodes and a plurality of conductive films, each of said plurality of conductive films having different thicknesses and being formed between said pair of electrodes in parallel.

7. A device for detecting a deterioration due to the grain growth in an inorganic material constituting a sample body, comprising:

a conductive sensor comprising a pair of electrodes and a conductive film disposed between said pair of electrodes, said conductive film being composed of a conductive material formed in a continuous region, for connecting electrically said pair of electrodes at least in an as-prepared state and having abrupt increase in the electric resistance due to the percolation transition in said conductive material in a predetermined deterioration state of said inorganic material caused by the grain growth of said conductive material accompanied by deterioration in said inorganic material.

8. A device as claimed in claim 7, wherein said inorganic material is noble metal.

9. A device as claimed in claim 7, wherein said conductive material is the same material as said inorganic material.

10. A device as claimed in claim 9, wherein said inorganic material is noble metal.

11. A device as claimed in clim 7, wherein said conductive sensor comprises a plurality of pairs of electrodes and a plurality of conductive films having different thicknesses, each of said plurality of conductive films being formed between each pair of said plurality of pairs of electrodes.

12. A device as claimed in claim 7, wherein said conductive sensor comprises a pair of electrodes and a plurality of conductive films each of said plurality of conductive films having different thicknesses, and being formed between said pair of electrodes in parallel.

* * * * *